United States Patent [19]

Muller-Rober et al.

[11] Patent Number: 5,538,879
[45] Date of Patent: Jul. 23, 1996

[54] EXPRESSION CASSETTE AND PLASMIDS FOR A GUARD CELL SPECIFIC EXPRESSION AND THEIR USE FOR THE INTRODUCTION OF TRANSGENIC PLANT CELLS AND PLANTS

[75] Inventors: Bernd Muller-Rober; Uwe Sonnewald; Lothar Willmitzer, all of Berlin, Germany

[73] Assignee: Institut fur Genbiologische Forschung Berlin GmbH, Germany

[21] Appl. No.: 140,180

[22] PCT Filed: Mar. 3, 1993

[86] PCT No.: PCT/EP93/00489

§ 371 Date: Jan. 24, 1994

§ 102(e) Date: Jan. 24, 1994

[87] PCT Pub. No.: WO93/18169

PCT Pub. Date: Sep. 16, 1993

[30]  Foreign Application Priority Data

Mar. 4, 1992 [DE] Germany .......................... 42 07 358.8

[51] Int. Cl.$^6$ ............................ C12N 15/82; C07H 21/04; A01H 5/00
[52] U.S. Cl. .................................... 435/172.3; 435/240.4; 435/320.1; 536/24.1; 800/205
[58] Field of Search ......................... 536/24.1; 800/205; 435/172.3, 240.4, 320.1

[56]  References Cited

PUBLICATIONS

Dupree et al 191 (Jul.) The Plant Journal 1(1): 115–120.
Outlaw et al 1984 Plant Physiol 74:424–429.
Terryn et al 1993 (Dec.) The Plant Cell 5:1761–1769.

Muller–Rober et al 1994 The Plant Cell 6:601–612.

Samac, D. A., et al, "Developmental and Pathogen–Induced Activation of the Arabidopsis Acidic Chitinase Promoter", The Plant Cell, vol. 3, No. 10, Oct. 1991, Rockville, Maryland, pp. 1063–1072.

Mueller–Roeber, B. T., et al, "One of Two Different ADP-–Glucose Pyrophosphorylase Genes From Potato Responds Strongly to Elevated Levels of Sucrose", Molecular & General Genetics, vol. 224, 1990, pp. 136–146.

Nakata, P. A., et al, "Comparison of the Primary Sequences of Two Potato Tuber ADP–Glucose Pyrophosphorylase Subunits", Plant Molecular Biology, vol. 17, No. 5, Nov. 1991, Dordrecht, The Netherlands, pp. 1089–1094.

Anderson, J. M., et al, "Molecular Characterization of the Gene Encoding a Rice Endosperm–Specific ADP Glucose Pyrophosphorylase Subunit and its Developmental Pattern of Transcription", Gene, vol. 97, No. 2, 1991, Amsterdam, The Netherlands, pp. 199–206.

*Primary Examiner*—Patricia R. Moody
*Attorney, Agent, or Firm*—Ostrolenk, Faber, Gerb & Soffen

[57]  ABSTRACT

A method of and plasmids for producing specific gene expression in the guard cells of plants. In particular, 5' transcriptional regulatory promoter regions are provided for guard cell specific expression. In addition, methods for preparing an expression cassette, plasmids, and the use of the cassettes and plasmids to produce transgenic plant cells and plants are described.

28 Claims, 5 Drawing Sheets

5'.........AAGCTTCGTAAAGAATATT
                HindIII

TTATCATAGTAAAACATGATTATCAAGTAAAAGTGAACAAGGGAGTA

ATATGAAGATTTATCATGTATTAAAAGCTCAATAGTGATTATAATTT

GAGGGACTAAAATAAATTTAAGGAGTTGTTAATATATTCCGAGAAAATA

AAATATTGTTTAAGTAGAAAAGTTATGGGGTGTATAAGTTAAATAATA

ATATTTTGTAAATAGGGATATGAGAAATGAGTATAAATAGAAAGATAGC

AAGGTTTCTCGTGAGAGTTCACAAGCCAATAAAGCTGATCACACTCCC

CTTTGTATGTCCACTCAACAACACTTCTTGTGATTCACTTTCAAT

TCTAGATCGGGGATCCCCGGGTGGTCAGTCCCCTT ATG TTA .....
  "BglII/SmaI"    SmaI                β-Glucuronidase
         BamHI

FIG. 2

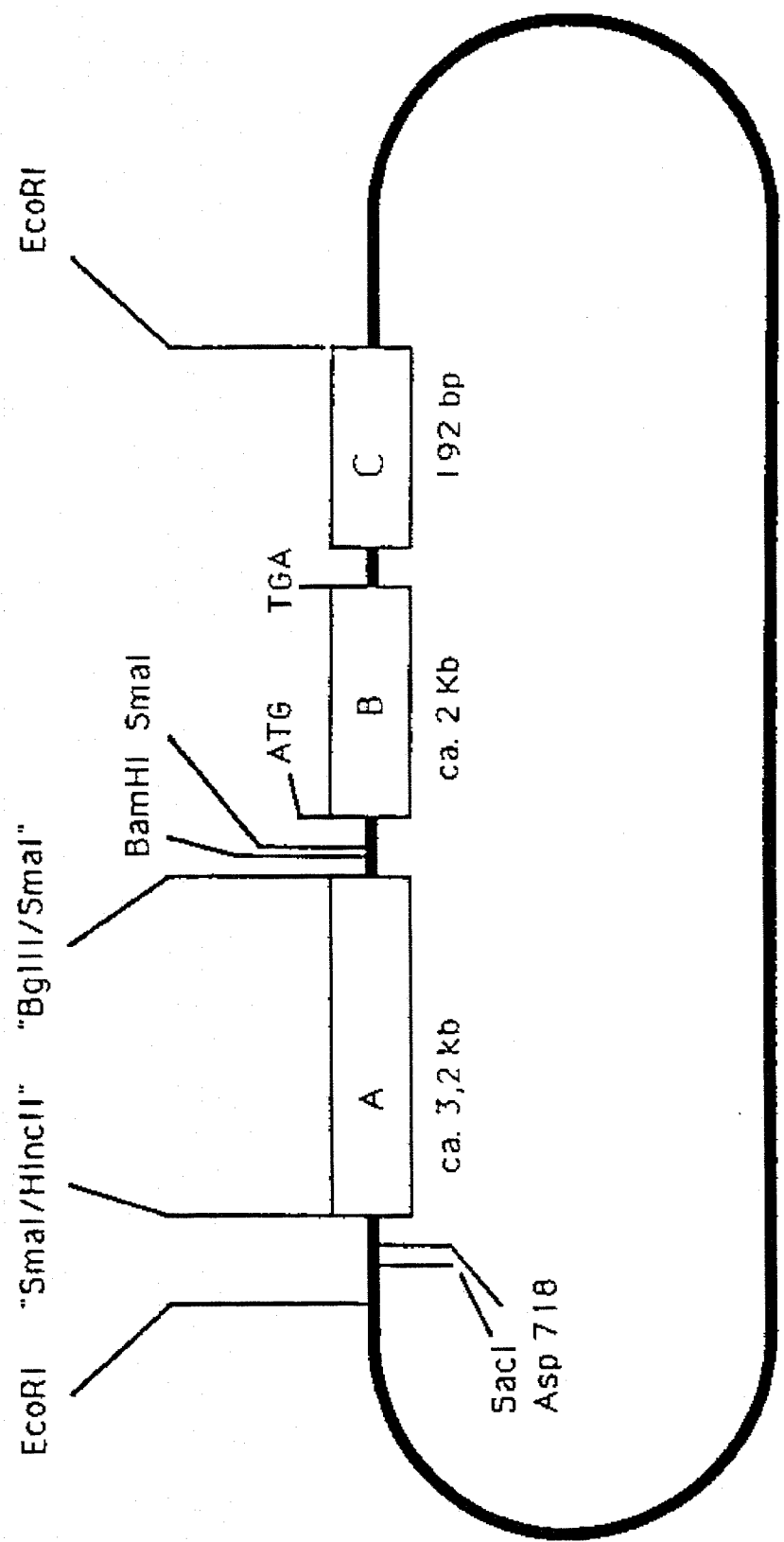

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 371 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Solanum tuberosum

-continued (vii) IMMEDIATE SOURCE:
  (A) LIBRARY: DNA library in phage EMBL 3

(ix) FEATURE:
  (A) NAME/KEY: TATA_signal
  (B) LOCATION: 242
  (D) OTHER INFORMATION: /note="TATA Box at 242"

(ix) FEATURE:
  (A) NAME/KEY: misc_feature
  (B) LOCATION: 1
  (D) OTHER INFORMATION: /note="HindIII cleavage site at 1"

(ix) FEATURE:
  (A) NAME/KEY: misc_feature
  (B) LOCATION: 371
  (D) OTHER INFORMATION: /note="BamHI cleavage site at 371"

(ix) FEATURE:
  (A) NAME/KEY: promoter
  (B) LOCATION: 1..371
  (D) OTHER INFORMATION: /note="guard cell specific promoter"

(xi) SEQUENCE DESCRIPTION: SEQ ID NO:1:

| | | | | | | |
|---|---|---|---|---|---|---|
| AAGCTTCGTA | AAGAATATTT | TATCATAGTA | AAACATGATT | ATCAAGTAAA | AGTGAACAAA | 60 |
| GGGAGTAATA | TGAAGATTTA | TCATGTATTT | AAAAGCTCAA | TAGTGATTAT | AATTTGAGGG | 120 |
| ACTAAATAAA | TTTAAGGAGT | TGTTAATATA | TTCCGAGAAA | ATAAAATATT | GTTTAAGTAG | 180 |
| AAAAGTTATG | GGGTGTATAA | GTTAAATAAT | AATATTTTGT | AAATAGGGAT | ATGGAAATGA | 240 |
| GTATAAATAG | AAAGATAGCA | AGGTTTCTCG | TGAGAGTTCA | CAAGCCAATA | AAGCTGATCA | 300 |
| CACTCCCCTT | TGTATGTCCA | CTCAACAACA | CAACTTCTTG | TGATTCACTT | TCAATTCTAG | 360 |
| ATCGGGGATC | C | | | | | 371 |

EXPRESSION CASSETTE AND PLASMIDS FOR A GUARD CELL SPECIFIC EXPRESSION AND THEIR USE FOR THE INTRODUCTION OF TRANSGENIC PLANT CELLS AND PLANTS

BACKGROUND OF THE INVENTION

The present invention relates to an expression cassette and plasmids containing this expression cassette. The DNA sequence of the expression cassette contains a transcriptional regulatory starter region, that ensures a specific gene expression in the guard cell of the leaves of plants, and no expression in mesophyllic cells or epidermal cells of the leaves. The invention further relates to a process for the preparation of transgenic plant cells, which contain sequences of the expression cassette as well as the use of the plasmids containing expression cassette for the preparation of transgenic plants.

Because of the continual growth in world population, there is a continual growing demand for nutrient and raw materials and, because of the foreseeable long-term limitation of agricultural land, it is the continuing task of biotechnological research to strive for the production of high yielding ecologically acceptable crops. To achieve this, the metabolism of plants has to be modified. This can be achieved, among other ways, by altering the DNA in the cell nucleus. The process for genetic modification of dicotyledenous and monocotyledenous is already known, (see for example Fraley, R. T. (1989) Science 244: 1293–1299; and Potrykus (1991) Ann Rev Plant Mol Biol Plant Physiol 42: 205–225).

SUMMARY OF THE INVENTION

With the present invention it is possible to influence the transpiration process and the gas exchange of a plant in regard to the increase of yield through manipulation of the genes which are expressed specifically in guard cells. This is not practicable using known expression systems because of the wide-ranging consequences of a non-guard cell specific gene expression for the total material exchange of the plant. An increase in yield of crop plants can be achieved by changing the photosynthesis activity of plants or by reducing the water needs. For this the guard cells of the epidermis of the leaf tissue are a valuable starting point.

Guard cells are specific kidney-shaped cells of that part of the epidermis which is above ground and in the air surrounding the green parts of higher plants and which are arranged in pairs and have a gap (hole) between each other. The stomata interrupts the otherwise continuous film of epidermis cells and causes the connection between the outer air and the intercellular system. In most plants the pore area resulting from the open holes occupies around 0.5 to 1.5% of the leaf area. Owing to their special formation, guard cells can so regulate their shape through active turgidity changes that the hole between them closes or opens. The openings are thus regulators of exchange, especially transpiration. The guard cells therefore have the task to so regulate the diffusion resistance, that the water demand through transpiration and $CO_2$ uptake for photosynthetic or darkness-$CO_2$ fixation, is in an appropriate relationship for the particular requirements. The opening or closing of the guard cells is led back to a change in the turgidity in the guard cells themselves and with it to the building up of a difference of the turgidity in the guard cells to that in the bordering epidermal cells (neighbouring cells).

Guard cells control the gas exchange between carbon dioxide uptake and transpiration (expiration of water vapour). Besides the concentration of carbon dioxide and the phytohormones, a constituent of the control system is the concentration of dissolved substances since these lead via changes in turgidity to the opening and closing of the holes. Since the changes of concentration in dissolved substances have wide-reaching consequences for the metabolism of plants, whether this occurs in tissues or cells, it is desirable to allow these changes only in certain areas of plants or during a certain time period in the plant growth cycle. It should be especially possible to achieve a change in carbon dioxide content or in the content of osmotically active substance of the guard cells thereby influencing the gas exchange and which is independent of the concentration of these substances in mesophyllic cells. For this reason, there is a great interest in the identification and the economic use of regulatory DNA sequences of plant genomes which are responsible for the specific transcription in guard cells.

With the help of guard cell specific regulatory sequences, by expression of suitable, newly introduced genes or by modulation of endogenous gene products, a permanent opening or closing or lengthening or shortening of the opening period of guard cells can be introduced.

The present invention provides a guard cell specific expression system with which such effect are possible.

Permanent opening of the guard cells should, on account of an increased transpiration, lead to a higher water loss in the plants which can, for example, in late phases of the growth cycle be desirable for the acceleration of the ripening of crops. Besides this, the production of strongly transpirationally active plants can result in the controlled drainage of soil. Plants rooting above ground can cause, by a lowering of the heat capacity of the soil, an earlier warming of growing areas and so make possible an earlier sowing of temperature-sensitive crops such as, for example, sugar beet. Since the first introduced genetically modified help plants are handicapped in the later phases of the growth cycle, they do not lead to a hindering of the development of crops, but on the contrary through an extension of the vegetation phase, to an increase in yield.

A wide-ranging closed holding of the hole openings (stomata) should cause, through a reduced gas exchange, a delayed growth and, as a result, timely extension of the vegetation phase. This can be of interest in ornamental crops. Further, agriculturally useful crops can be produced which as transpiration weak soil cover, prevent an erosion of useful land in the quiet phase or at the beginning of the vegetation phase of crops.

A change in the opening period of the holes (stomata) has been shown to be valuable in crops. For example, in green harvested plants, especially fodder crops, retention of water prevents the drying out of older leaf material and thereby increases the yield. Further, an adaptation to an area with increased atmospheric carbon dioxide concentration (for example adding $CO_2$ in greenhouses), can be envisaged. Through artificial lengthening of the opening period, effects such as mineral deprivation in reduced transpiration, following a higher carbon dioxide partial pressure in the plants, can be compensated for.

By combination of guard cell specific regulatory elements with other control systems, further use possibilities can be seen. For example, through a coupling of chemical sensors, a closing of the hole openings (stomata) induced from outside of the hole openings (stomata) can be produced, thereby providing a growth stop of certain plants, in particular agriculturally useful plants, so that they can could be produced at a desired time.

In order to specify regulatory DNA sequences, one must first seek products that appear only at certain times in the cell growth cycle or in a certain part of the plant such as in guard cells. Once the responsible gene is identified and isolated, it is necessary to have a basic investigation of the sequence and above all the identification and isolation of the desired transcriptional regulatory region. Then a suitable model must be prepared whose validity can be proven by experiment.

There is now provided an expression cassette whose DNA sequence is supplied with a transcriptional regulatory starter region for guard cell specific gene expression which causes no expression in mesophyllic cells or epidermal cells of the leaves. With the expression cassette, a gene manipulation of plants is possible which causes a permanent opening or closing or a lengthening or shortening of the opening period of the guard cells.

The DNA sequence contains the transcriptional regulatory starting region for a guard cell specific gene expression.

On the expressions cassette there is located the DNA sequence of the guard cell specific promoter having the sequence (Seq. ID No:1)

agent, fusion of protoplasts, injection or electroporation of DNA etc. Where *Agrobacteria* are used for the transformation, the DNA being introduced must be cloned in special plasmids, and that means either in an intermediary or binary vector. The intermediary vectors, on the basis of sequences, which are homologous to sequences into the T-DNA, can be integrated by homologous recombination in the Ti- or Ri-plasmid. The vector contains also the necessary vir-region for the transfer of the T-DNA. Intermediary vectors cannot be replicated in *Agrobacteria*. Using a helper plasmid, the intermediary vector can be transferred to *Agrobacterium tumefaciens* (conjugation). Binary vectors can be replicated in E. coli as well as in *Agrobacteria*. They can contain a selection marker gene and a linker or polylinker, which are framed by the right and left T-DNA border regions. They can be directly transformed in the *Agrobacteria* (Holsters et al. (1978) Mol Gen. Genet. 163: 181–187). The *Agrobacteria* serving as host cells should contain a plasmid, that carries a vir-region. The vir-region is necessary for the transfer of the T-DNA into the plant cells. Additional T-DNA can be contained. The so transformed bacterium is used for the transformation of plant cells. For the transfer of the DNA into the plant cells, plant-explantate can suitably be cocultivated with *Agrobacterium tumefaciens* or *Agrobacterium rhizogenes*. From the infected plant material (e.g. leaf

| HindIII | | | | | |
|---|---|---|---|---|---|
| AAGCTTCGTA | AAGAATATTT | TATCATAGTA | AAACATGATT | ATCAAGTAAA |
| AGTGAACAAA | GGGAGTAATA | TGAAGATTTA | TCATGTATTT | AAAAGVTCAA |
| TAGTGATTAT | AATTTGAGGG | ACTAAATAAA | TTTAAGGAGT | TGTTAATATA |
| TTCCGAGAAA | ATAAAATATT | GTTTAAGTAG | AAAAGTTATG | GGGTGTATAA |
| GTTAAATAAT | AATATTTTGT | AAATAGGGAT | ATGGAAATGA | GTATAAATAG |
| AAAGATAGCA | AGGTTTCTCG | TGAGAGTTCA | CAAGCCAATA | AAGCTGATCA |
| CACTCCCCTT | TGTATGTCCA | CTCAACAACA | CAACTTCTTG | TGATTCACTT |
| TCAATTCTAG | ATCGGGGATC | C | | |

BamHI (see also Example 4)

Plant cells, that contain a regulatory region for a guard cell specific gene expression, can be prepared by the following process:

a) Isolation of the clone GS 6–11 as described in Examples 1 and 2. The clone contains an approximately 12 kb size DNA-fragment, that contains a guard cell specific regulator element (see FIG. 1).

b) preparation of the plasmid pSF-6 corresponding to Example 3 using the approximately 12 kb size SalI-fragment of the clone GS 6–11.

c) preparation of the plasmid pH 6-1 using the approximately 5.3 kb size HincII-fragment of the plasmid pSF-6 corresponding to Example 3.

d) preparation of the plasmid pAS (DSM 6906), pAS-GUS (DSM 6907) and/or pS1 - D4GUS, using the approximately 3.2 kb size HincII/BglII-fragment of the regulatory starter-region of the ADP glucose pyrophosphorylase gene of *Solanum tuberosum* from the plasmid pH 6-1 (Example 3). The plasmid pAS-GUS contains in addition to the sequence of the plasmid pAS, the coding region of the β-glucuronidase gene.

e) transfer of the T-DNA of the plasmid pAS (DSM 6906), pAS-GUS (DSM 6907) and/or pS1 - D4GUS, in a plant cell.

For the introduction of DNA into a plant host cell there are many techniques available. These techniques include the transformation with T-DNA using *Agrobacterium tumefaciens* or *Agrobacterium rhizogenes* as a transformation pieces, stem segments, roots and also protoplasts or suspensions of cultivated cells), whole plants can be regenerated in a suitable medium, which contain antibiotics or biocides for selection. The resulting plants can then be tested for the presence of introduced DNA. No special demands are placed on the plasmids used in injection and electroporation. Simple plasmids such as e.g. pUC-derivatives can be used. Should however whole plants be regenerated from such transformed cells, the presence of a selectable marker gene is necessary.

The plasmids pAS and pAS-GUS have a size of around 13.3 and 15.2 kb respectively and each contain the approximately 2.0 kb size kanamycin resistance gene, the approximately 3.2 kb size HindII/BglII-promoter-fragment of the regulatory starter-region of the ADP-glucose-pyrophosphorylase-gene GS6–11 of *Solanum tuberosum*, a linker and a transcription terminator of the nopaline synthase gene. The plasmid pAS-GUS contains also the approximately 2 kb size β-glucuronidase gene.

For the preparation for the introduction of foreign genes into higher plants, a large number of cloning vectors are available, which contain a replication signal for E. coli and a marker, which allows for the selection of the transformed cells. Examples of vectors are pBR 332, pUC-series, M13 mp-series, pACYC 184 etc. The desired sequence can be introduced in the vector on a suitable restriction position. The resulting plasmid is used for the transformation in E. coli. The E. coli cells are cultivated in a suitable nutrient medium, then harvested and lysed. The plasmid is reextracted. For analysis in general, a sequence analysis, a restriction analysis, electrophoresis and other biochemicalmolecular biological methods can be used. After each manipulation, the used DNA-sequence can be split and attached to another DNA-sequence. Each plasmid sequence can be cloned in the same or different plasmids. Depending on the method of introduction of the desired gene into the plant, further DNA-sequences may be necessary. Should for example the Ti- or Ri-plasmid be used for the transformation of the plant cells, at least the right boundary, and often however, the right and the left boundaries of the Ti- and Ri-plasmid T-DNA, should be linked as a flanking area of the introduced gene.

The use of T-DNA for the transformation of plants cells has been intensively researched and is well described in EP 120 516; Hoekema, In: The Binary Plant Vector System, Offset-drukkerij Kanters B. V., Alblasserdam, (1985), Chapter V; Fraley, et al., Crit. Rev. Plant Sci., 4:1-46 and An et al. (1985) EMBO J. 4: 277–287.

Once the introduced DNA is integrated in the genome, it is generally stable there and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow for the selection of transformed cells from cells which lack the introduced DNA.

The transformed cells grow within the plants in the usual manner (see also McCormick et al. (1986) Plant Cell Reports 5: 81–84). These plants can be grown normally and crossed with plants, that possess the same transformed genes or different. The resulting hybrid individuals have the corresponding phenotypical properties.

Two or more generations should be grown to ensure that the phenotypic characteristic remains stabile and inherited. Also seeds should be harvested to ensure that the corresponding phenotype or other individualities remain. All plant species are suitable as host plants for the guard cell specific expression, but especially crop species.

Suitable crops are e.g. potatoes, tobacco, tomatoes and sugar beet as well as species which are agricultural supplementary crops e.g nitrogen providing crops.

Further DNA sequences which contain information for the formation and quantitative distribution of endogenous products or the formation of exogenous expression products can be fused to the DNA sequence of the expression cassette of the invention.

Endogenous expression products are e.g. phytohormones, carbohydrates and other metabolites. Heterologous products are e.g. carbohydrates not naturally formed in plants or enzymes for the liberation of substances with phytohormone activity as a primary step, which are not naturally converted to phytohormones in plants.

The DNA sequences that can be inserted after the regulatory sequence of the expression cassette should contain all possible open reading frames for a preferred peptide as well as one or more introns. As examples can be named: sequences for enzymes, sequences which are complementary:

a) to a genome sequence, whereby the genome sequence may be an open reading frame;

b) to an intron;

c) to a non-coding leader sequence;

d) to each sequence, which inhibits, upon integration in reverse orientation into the genome, the transcription, mRNA processing for example splicing) or the translation.

The desired DNA sequence can be prepared synthetically or extracted naturally or can consist of a mixture of synthetic and natural DNA constituents. In general, synthetic DNA sequences are produced with codons, which are preferred for plants. These preferred codons for plants can be selected from codons with the highest protein abundance, which are expressed in the most interesting plant species. In the preparation of an expression cassette, various DNA fragments can be manipulated in order to obtain a DNA sequence that reads suitably in the correct direction and which is supplied with the correct reading frame. For the combination of DNA fragments with each other, adaptors or linkers can be put onto the fragments.

Suitably, transcription start and termination region in the transcription direction should be provided with a linker or polylinker which contains one or more restriction positions for the insertion of this sequence. As a rule, the linker has 1 to 10, mostly 1 to 8 and preferably 2 to 6 restriction positions. In general the linker has, within the regulatory region, a size of less than 100 bp, generally less than 60 bp and at least however 5 bp. The transcriptional initiation area as well as being native and/or homologous can also be foreign and/or heterologous to the host plants. The expression cassette comprises in the 5'-3' transcription direction, a region for the initiation of transcription for the plant, a preferred sequence and a region for the transcriptional termination. Various termination areas are exchangeable, preferably with each other.

Further, manipulations which prepare suitable restriction cutting sites or separate the excess DNA or cutting positions, can be carried out. Where insertions, deletions or substitutions, for example transitions and transversions are to be considered, in vitro-mutagenesis, primer repair, restriction or ligation can be used. In suitable manipulations, such as for example restriction, chewing back or filling in of overhangs for blunt ends, complementary ends of the fragments for the ligation can be used. For carrying out the various stages, cloning is useful for an enlargement of the DNA amounts and for the DNA analysis which ensures the expected success of the introduction.

For the introduction of foreign genes into plants by using the guard cell specific regulatory sequence, a number of possibilities are available, but especially interesting is however, the expression of genes which change the regulation of the guard cell in relation to the gas exchange as well as the expiration of water vapour (transpiration).

For the expression of such genes the use of the expression cassette of the invention is especially valuable.

A modification of the guard cells with effects on the opening condition of the stomata can be achieved in two ways: through a modulation of the content of endogenous proteins, enzymes, carriers or pumps which transport metabolite through membranes, present in the guard cells; or through the transfer and expression of genes of homologous or heterologous or of synthetic origin, which encode proteins, enzymes, carrier or pumps, which do not belong to the normal constituents of a guard cell, but whose activity or presence influences the state of the cells in relation to the opening of the stomata.

For regulation of the transpiration three sensor systems are concerned: sensors for measuring the carbon dioxide concentration, phytohormone sensors and a measuring system for turgidity gradients between guard cells and bordering epidermal cells. Turgidity changes are for example possible through influencing the activity of enzymes or transport systems of the carbohydrate metabolism. Besides a direct change of the concentration of the osmotic activity of the carbohydrate, for example by means of cytosolic or vacuolar invertases or of the chloroplast triose phosphate translocators, consequences for the osmo regulation have to be expected, through an enrichment or reduction of precursors of osmotically active substances. For example, by modifying the ADP glucose pyrophosphorylase activity, starch synthesis can be influenced, and so the amounts on substrates for glycolysis and citrate cycle can be modified, whereby lastly the concentration of the malate, a substance of importance in relation to the cell turgidity, is concerned. An increase of the apoplastic invertase activity in guard cells can raise the starch concentration by an increased uptake of hexoses. Such an introduction must follow guard cell specificity since an increase of apoplastic invertase activity in the strongly photosynthetic active mesophyllic cells leads to a reduction of the assimilate transport and along with it a higher osmotic: loading of the tissues (see Schaewen et al 1990 EMBO J 9: 3033–3044). Further, an increase of the expression or the expression of a modified phospho-enol-pyruvate carboxylase can be envisaged. The enzyme catalyses the reaction of phospho-enol-pyruvate to oxaloacetate, that again is a precursor for malate. Besides, proton pumps (proton-ATPases) can contribute to a change of the osmotic potential, which makes possible the ion transport process for the electrochemical gradients.

Further possibilities of influence are seen in the activity of the carbonate dehydratase, which controls the equilibrium between dissolved carbon dioxide and carbonate in so far as it thus influences the cellular carbon dioxide concentration; but also for example in fructose-biphosphatase which contributes as an enzyme in the regenerative section of the Calvin cycle in the fixing of carbon dioxide.

The expression cassette of the invention can also be used for guard cell specific expression of genes which regulate the phytohormone level of plants.

Local changes to the phytohormone level are especially interesting for the influencing of the properties of guard cells. For example auxins cause an opening of the stomata, application of abscisic acid leads to a fast closing of the stomata. Numerous genes whose products have influence in the hormone make-up of plants, have already been cloned, (see e.g. Klee, H. & Estelle, M. (1991) Ann Rev Plant Physiol Plant Mol Biol 42: 529–551). The genes 1 and 2 of the T-DNA of *Agrobacterium tumefaciens* code for auxin synthesis enzyme, while the indole acetate lysine synthetase (Romano et al. (1991) Genes & Development 5: 438–446) catalyses the inactivation of auxins. Cytokinins are liberated through a glucosidase encoded by the rol c gene of the T-DNA from *Agrobacterium rhizogenes* (Estruch et al. (1991) EMBO J 10: 3125–3128); the gene product of the T-DNA gene 6b of A. tumefaciens reduces cytokinin activity (Spanier et al. (1989) Mol Gen Genet 219: 209–216). Ethylene production can be stimulated in plants by expression of the aminocyclopropane carboxylate synthase and (Huang et al. (1991) Proc Nat Acad Sience 88: 7021–7025); inhibition of the aminocyclopropane carboxylate oxidase by expression of antisense-RNA which depresses the ethylene liberation.

Because of the wide-reaching consequences of hormonal activity for the plants an influence of the guard cell activity is feasible only by using the expression cassette of the invention for a guard cell specific gene expression.

Processes for the reduction of the activity and/or the amount of a specified enzyme are already known in the art. For this purpose, a chimeric gene is introduced into the plant. It consists of a promoter active in the plant, a coding sequence of the enzyme whose activity is reduced is fused to the promoter in the anti-sense direction, (3'-end of the coding sequence to the 3'-end of the promoter) and a termination signal, functional in plants, for transcription. For introduction of genes of this kind in plant cells there are various processes available. From the transformed cells, intact transgenic plants can be regenerated for which the desired phenotype (lowering of the activity of the target enzyme) must be determined.

The identification of necessary transcriptional starting regions can be achieved in a number of ways. As a rule mRNA which is isolated from certain parts of the plants (here, guard cells) is used (see also Example 1). For an additional increase in concentration of the mRNA characteristic of the tissue or the plant state, cDNA can be prepared whereby unspecific cDNA is attached to the mRNA or the cDNA from other tissues (mesophyllic cells) or plant states. The remaining cDNA can be used then for the probing of the genome of the complementary sequences using a suitable plant DNA library.

Where a protein, appearing in a specific cell or tissue type, is isolated it can be partially sequenced so that a probe can be prepared for direct identification of the corresponding sequences in a plant DNA library (see Example 2). Then the sequences that hybridise with the probe can be isolated and manipulated. Further, the non-translated 5' region that is associated with the coding region can be isolated and tested in expression cassettes for transcriptional activity.

The expression cassettes obtained, which use the non-translated 5' regions can be transformed in plants (see above) where their functionality as transcriptional regulators in combination with a heterologous structure gene (other than the open reading frame of the wild type genes that is associated with the non-translated 5' region) as well as the guard cell specificity can be tested. In this way sequences, which are necessary for the guard cell specific transcription, can be identified.

The following plasmids were deposited at the Deutschen Sammlung yon Mikroorganismen (DSM) in Braunschweig, Germany on the 13.02.1992 (deposit number):

Plasmid pAS (DSM 6906);

Plasmid pAS-GUS (DSM 6907).

DESCRIPTION OF THE FIGURES

The file of this patent contains at least one drawing executed in color. Copies of this patent with color drawing(s) will be provided by the U.S. Patent and Trademark Office upon request and payment of the necessary fee.

FIG. 2 shows the promoter GUS fusion of the plasmid pAS-GUS, that contains the nucleic acid sequence of a part of the important areas for transcriptional regulation of the ADP glucose pyrophosphorylase gene GS6–11, which is also contained in Plasmid pAS. ATG signifies the translation start for the β-glucuronidase. The Bgl II cutting site, where the clone pH6-1 is cut and attached with the linearised plasmid pUC 19 to the SmaI cutting site, is shown. The sequence up to the BamHI cutting site stems from the polylinker of pUC 19 and the following nucleotide from the plasmid pBI101.1 (Jefferson et al. (1987) Plant Mol Biol Rep 5: 387–405). The corresponding region with der cDNA is shown in bold lettering. The two first codons of β-glucuronidase are bracketed. A sequence, which possibly represents a Hoghess box, is underlined.

A=Fragment A (approximately 3.2 kb): contains:

nt 400–414 from pUC 19 approximately 3.2 kb from GS6-11 nt 415–421 from pUC 19

C=Fragment C (192 bp): contains nt 11749–11939 from pTiACH5 (Gielen et al. (1984) EMBO J 3: 835–846)

FIG. 4 shows the approximately 15.2 kb size plasmid pAS-GUS, that is a derivative of pBI101.1 (Jefferson et al. (1987) Plant Mol Biol Rep 5: 387–405). The plasmid pBI101.1 again is a derivative of pBIN 19, that contains, at nt 2534, an insertion of 1.87 kb of the coding region of β-glucuronidase (B). Plasmid pAS-GUS differs from pAS by this insertion. In detail pAS-GUS contains the following fragments:

A=Fragment A (approximately 3.2 kb): contains:

nt 400–414 from pUC 19 approximately 3.2 kb from GS6-11 nt 415–421 from pUC 19

B=Fragment B (1.87 kb): coding region of the β-Glucuronidase.

C=Fragment C (192 bp): contains nt 11749–11939 from pTiACH5 (Gielen et al. (1984) EMBO J 3: 835–846)

Figure 5A:
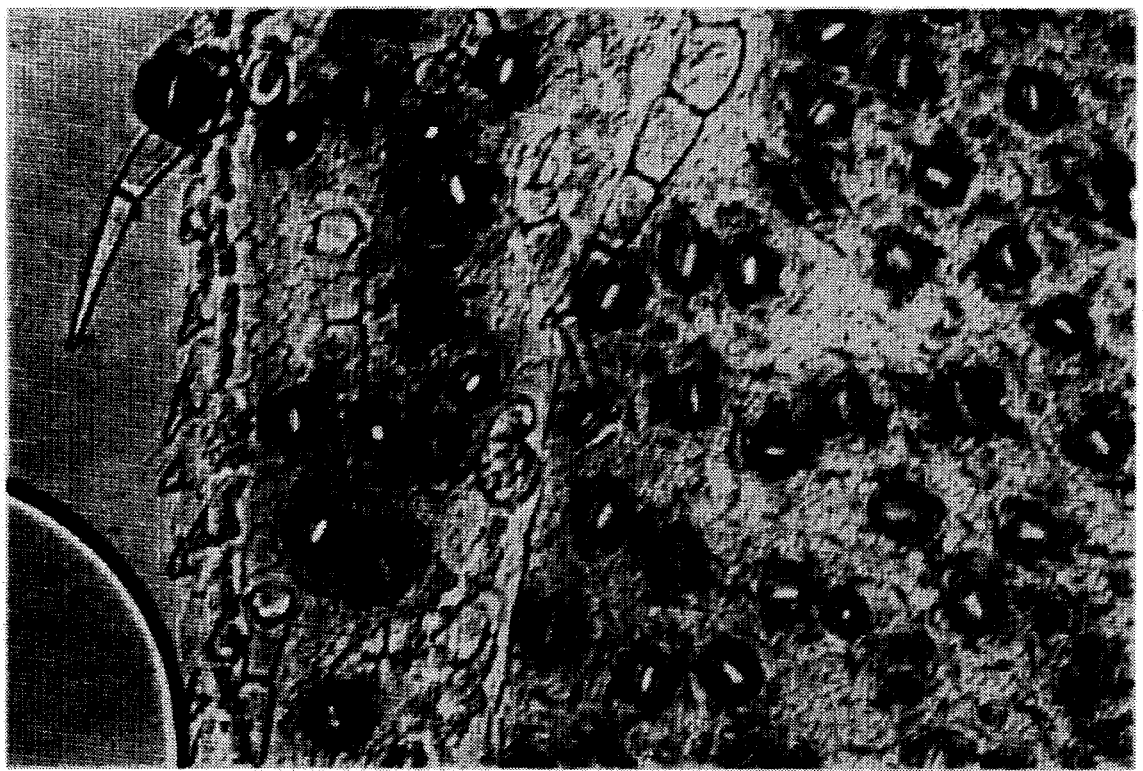
Figure 5B:
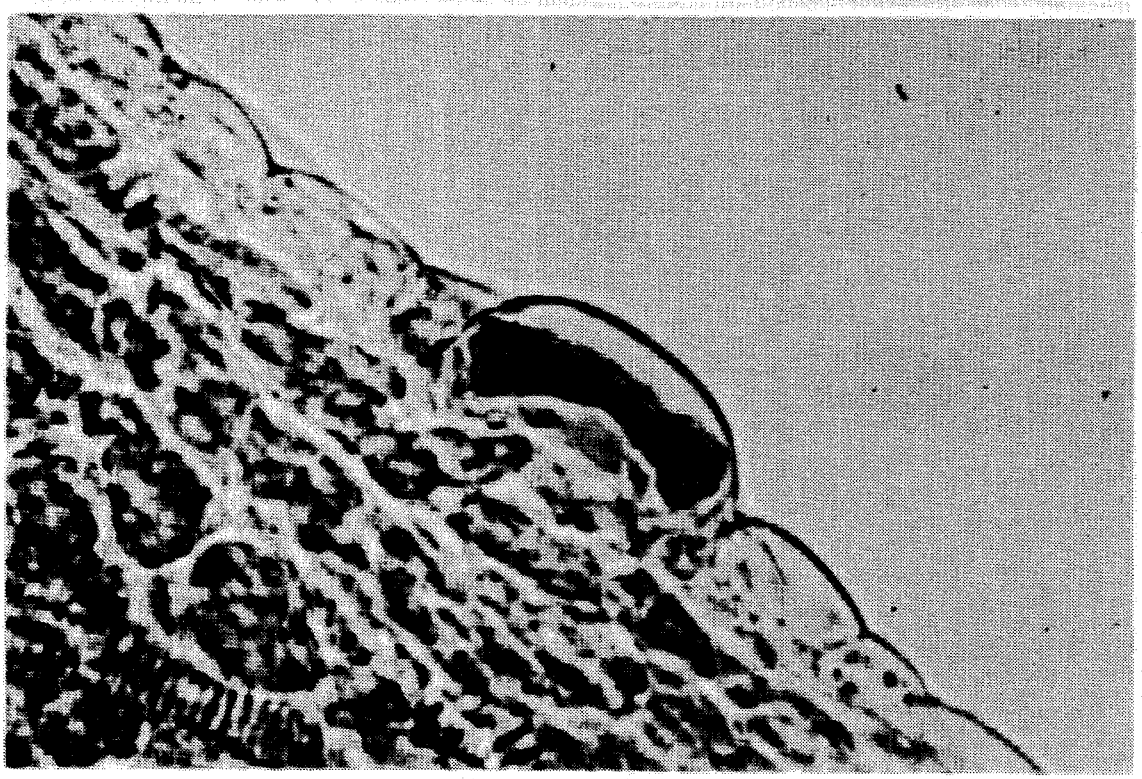

FIGS. 5A and 5B are a top and side view, respectively, of a leaf of a transgenic potato plant transformed with the plasmid pAS-GUS wherein the blue areas show β-glucuronidase expression. It can clearly be seen, that no expression in the mesophyllic cells or epidermis cells is detectable but only a specific expression in the guard cells.

In order to understand the examples forming the basis of this invention all the processes necessary for these tests and which are known per se will first of all be listed:

1. Cloning process

The vectors pUC 18/19 and M13mp10 series (Yanisch-Perron et al. (1985) genee 33: 103–119), as well as the vector EMBL 3 (Frischauf et al. (1983) J Mol Biol 170: 827–842) were used for cloning.

For plant transformations, the gene constructions were cloned into the binary vector BIN 19 (Bevan (1984) Nucl. Acids Res 12: 8711–8720).

2. Bacterial strains

The *E. coli* strain BMH71-18 (Messing et al., Proc. Natl. Acad. Sci. USA (1977), 24, 6342–6346) or TB1 was used for the pUC and M13 mP vectors.

For the vector BIN19 exclusively the *E. coli* strain TB1 was used. TB1 is a recombinant-negative, tetracycline-resistant derivative of strain JM101 (Yanisch-Perron et al., genee (1985), 33, 103–119).

The genotype of the TB1 strain is (Bart Barrel, personal communication): F' (traD36, proAB, lacI, lacZΔM15), Δ(lac, pro) , SupE, thiS, recA, Srl::Tn10 (TcR).

The transformation of the plasmids into the potato plants was carried out by means of the *Agrobacterium tumefaciens* strain LBA4404 (Bevan, M., Nucl. Acids Res. 12, 8711–8720, (1984); BIN19 derivative).

3. Transformation of *Acrobacterium tumefaciens*

In the case of BIN19 derivatives, the insertion of the DNA into the agrobacteria was effected by direct transformation in accordance with the method developed by Holsters et al., (Mol. Gen. Genet. (1978), 163, 181–187). The plasmid DNA of transformed agrobacteria was isolated in accordance with the method developed by Birnboim and Doly (Nucl. Acids Res. (1979), 7, 1513–1523) and was analysed by gel electrophoresis after suitable restriction cleavage.

4. Plant transformation

Ten small leaves, wounded with a scalpel, of a sterile potato culture were placed in 10 ml of MS medium with 2% sucrose containing from 30 to 50 μl of an *Agrobacterium tumefaciens* overnight culture grown under selection. After from 3 to 5 minutes of gentle shaking, the Petri dishes were incubated in the dark at 25° C. After 2 days, the leaves were laid out on MS medium with 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% Bacto agar. After incubation for one week at 25° C. and 3000 lux, the claforan concentration in the medium was reduced by half.

5. Analysis of genomic DNA from transgenic potato plants

The isolation of genomic plant DNA was performed in accordance with Rogers and Bendich (Plant Mol. Biol. (1985), 5, 69–76. After suitable restriction cleavage, 10 to 20 μg of DNA were tested by means of Southern blots for the integration of the DNA sequences to be introduced.

6. β-Glucuronidase-Activity test (GUS-Assay)

The β-glucuronidase is a bacterial enzyme, that hydrolyses β-glucuronide and is accessible to quantitative as well as histochemical activity determinations. Activity measurement were carried out by the method of Jefferson et al. (1987) EMBO J 6: 3901–3907. Tissue probes were incubated in 1 mM X-Gluc, 50 mM Na-phosphate pH 7.0 and 0.1% Tween 20 bis until the desired intensity of blue colouring has been achieved.

The following examples illustrate the preparation of the expression cassette, whose DNA sequence contains a regulatory sequence for a guard cell specific gene expression. The introduction of the sequence in a plasmid is also illustrated in that a transformation of plant cells is possible. In addition, the regeneration of transgenic plants and the investigation of the function of the expression cassette in transgenic plants is shown.

EXAMPLE 1

Cloning and structure analysis of an ADP glucose pyrophosphorylase gene from *Solanum tuberosum* cDNA clones, that code for the S-subunit of ADP glucose pyrophosphorylase of potato, were isolated from the potato variety "Desirée" and sequenced (Müller-Röber et al. (1990) Mol Gen. Genet. 224:136–146; EP 455 316). These cDNA clones are used to isolate a homologous, genomic, ADP glucose pyrophosphorylase clone from the potato variety AM 80/5793 (Max-Planck-Institut for Züchtungsforschung, Köln).

EXAMPLE 2

Cloning, identification and primary structure of an ADP glucose pyrophosphorylase gene as a fragment of genomic DNA from *Solanum tuberosum*

Figure 1:
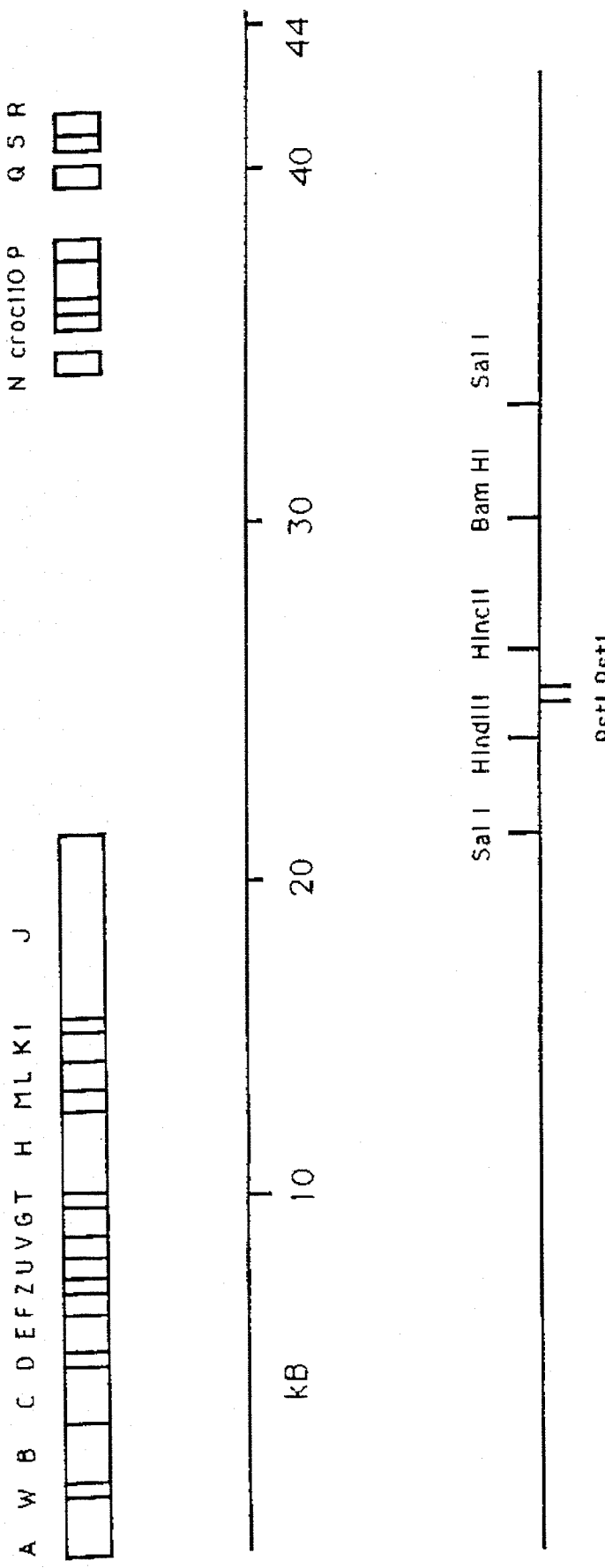
FIG. 1 shows the restriction map of the genomic clone GS6–11, which codes for the S-subunit of the ADP glucose pyrophosphorylase of *Solanum tuberosum*. Above the restriction map are the designations of genes of the phages Lambda as well as a scale for estimating the length of the DNA sequences in kilobases (kb).

A genomic library of the nuclear DNA from the potato variety AM 80/5793, which has been established in vector EMBL 3 derived from Lambda phages, was probed with the help of the ADP glucose pyrophosphorylase cDNA S25-1 (see. Example 1). Several independent clones were obtained, from which the clone GS6–11 was used for the further working. The restriction map of the clone GS6–11 is shown FIG. 1. Part of the gene was sequenced and the sequence is shown in FIG. 2.

EXAMPLE 3

Figure 3:
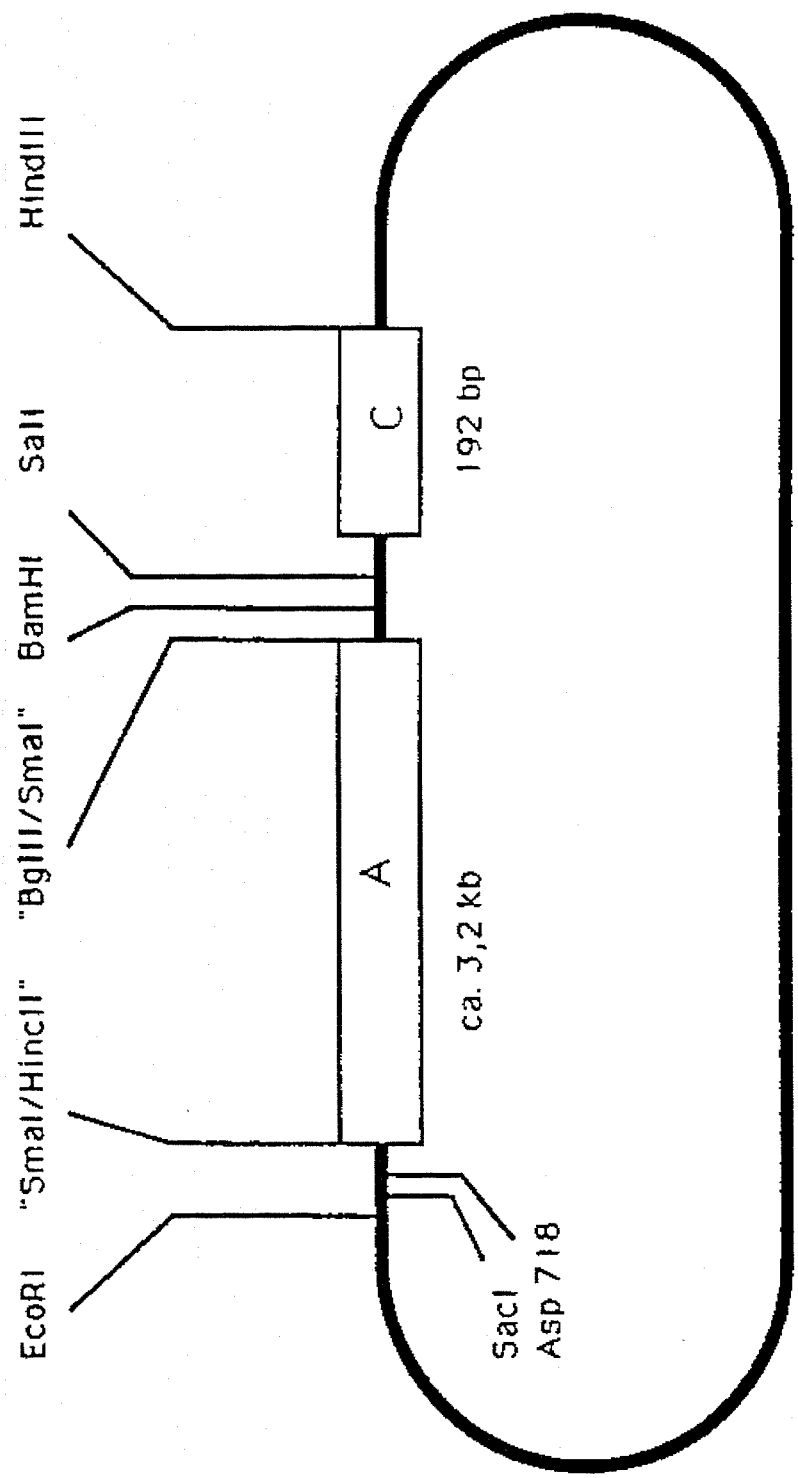
FIG. 3 shows the approximately 13.2 kb size Plasmid pAS. It contains the approximately 2.0 kb size kanamycin resistance gene as a constituent of the starting vector pBIN 19 (Bevan, M.(1984) Nucl Acids Res 12: 8711–8721), the approximately 3.2 kb size regulatory area for a guard cell specific gene expression from the ADP glucose pyrophosphorylase gene from *Solanum tuberosum* from the clone GS6-11 (A), inserted between nucleotide position (nt) 2525 and 2544 of pBIN 19 as well as the transcription terminator from the nopaline synthase gene (C), inserted at nt 2494 of pBIN 19.

Identification of the regulatory areas responsible for the guard cell specific expression of the ADP glucose pyrophosphorylase gene The greater than 12 kbp size Sal I insertion of the genomic clone GS6–11 was cloned in the Sal I restriction site of the vectors pUC 19 and the Plasmid SF-6 resulted. An approximately 5.3 kbp long HincII fragment of the plasmid SF-6 was sub-cloned in the HincII restriction site of the vectors pUC 19 and the Plasmid pH6-1 resulted. The approximately 3.2 kbp long HincII/Bgl II of the plasmid pH6-1 was cloned after filling in of the Bgl II restriction site in the SmaI cutting position of the vector pUC 19. In this way the 5'end for the EcoRI restriction site of the polylinker was orientated, so that the plasmid pSA was obtained. Then the EcoRI/BamHI fragment was cut from the pUC 19 derivative pSA and after filling in the EcoRI restriction site, was put in the vector pBI101.1 (Jefferson et al.(1987) Plant Mol Biol Rep 5: 387–405), whereby pAS-GUS was obtained (see FIG. 4). The vector pBI101.1 was previously cut HindIII/BamH I and the HindIII restriction site was filled in. The vector pBI101.1 contains the coding region of the β-glucuronidase gene as a reporter gene. The β-glucuronidase is indicative of a histological determination of its activity and can thus be introduced for the analysis of the cell specificity of a regulatory region of an expression system to be tested. In parallel with the cloning of pAS-GUS the expression vector pAS was prepared, which contains a polylinker between the promoter fragment of the ADP glucose pyrophosphorylase and the terminator of the octopine synthase gene (see. FIG. 3). With the help of this plasmid an expression of preferred genes under the control of the ADP glucose pyrophosphorylase promoters is possible.

The construct pAS-GUS, with the coding region of β-glucuronidase as reporter gene, was transferred into the *Agrobacteria* strain LBA 4404 (Bevan, M.(1984) Nucl Acids Res 12: 8711–8721) and the *Agrobacteria* containing the chimeric ADP glucose pyrophosphorylase/β-glucuronidase gene is used for transformation of potato and tobacco leaves.

Of ten resulting independent transformants, in which the presence of the intact, unrearranged chimeric ADP glucose pyrophosphorylase/β-glucuronidase gene had been proven with the help of southern blot analyses, leaves, stems, tubers and roots were tested for β-glucuronidase activity. The results are shown in FIG. 5. From these data it is clearly shown, that the HincII fragment of the ADP glucose pyrophosphorylase gene GS6–11, which was fused with the β-glucuronidase gene, had induced in the leaf a guard cell specific activity of the β-glucuronidase. This activity could not been seen in the mesophyllic and epidermis cells.

EXAMPLE 4

Further concentration of the regulatory regions responsible for the guard cell specific expression of the ADP glucose pyrophosphorylase gene The 0.35 kbp size HindIII/BamHI fragment was isolated from Plasmid pSA described in Example 3 and inserted in vector pBI101.1 which had been linearised with restriction enzymes BamHI and HindIII. The resulting plasmid bears the designation pS1-D4GUS. The 0.35 kbp size HindIII/BamHI insertion of the plasmid is shown in FIG. 2 as well as in Seq ID No 1. The vector pBI101.1 contains the coding region of the β-glucuronidase gene as reporter gene. The β-glucuronidase is indicative of a histological determination of its activity and can thus be introduced for the analysis of the cell specificity of a regulatory region of an expression system to be tested. The construct pS1-D4GUS with the coding region of β-glucuronidase as reporter gene, was transferred into the Agrobacteria strain LBA 4404 (Bevan, M.(1984) Nucl Acids Res 12: 8711–8721) and the *Agrobacteria* containing the chimeric ADP glucose pyrophosphorylase/β-glucuronidase gene is used for transformation of potato and tobacco leaves.

Of ten resulting independent transformants, in which the presence of the intact, unrearranged chimeric ADP glucose pyrophosphorylase/β-glucuronidase gene had been proven with the help of southern blot analyses, leaves, stems, tubers and roots were tested for β-glucuronidase activity. It was shown that the 0.35 kbp size HindIII/BamHI promoter fragment of the ADP glucose pyrophosphorylase gene has a comparable activity to that of the EcoRI/BamHI promoter fragment of the plasmid pSA (see. FIGS. 5A and 5B) in the stomata cells of leaves, while for vascular tissues, tubers and stolons of potato plants and roots no activity was seen.

We claim:

1. A recombinant double stranded DNA molecule comprising an expression cassette comprising:
  i) a 5' transcriptional regulatory region, wherein said 5' transcriptional regulatory region comprises the DNA sequence of Seq I.D. No. 1; and
  ii) a DNA fragment operably linked to said 5' transcriptional regulatory region, wherein said 5' transcriptional regulatory region leads to specific expression of said DNA fragment only in guard cells and not in mesophyllic or epidermal cells of leaves of transformed plants.

2. A recombinant double stranded DNA molecule according to claim 1, wherein said 5' transcriptional regulatory region is the 5' transcriptional regulatory region of a gene coding for ADP glucose pyrophosphorylase.

3. A recombinant double stranded DNA molecule according to claim 1, wherein said 5' transcriptional regulatory region is isolated from *Solanum tuberosum*.

4. A recombinant double stranded DNA molecule according to claim 1, wherein said 5' transcriptional regulatory region is the 3.2 kb HincII/BglII fragment contained in the plasmid pAS, deposited as DSM 6906.

5. A recombinant double stranded DNA molecule according to claim 1, wherein said DNA fragment is linked to the 5' transcriptional regulatory region in sense orientation.

6. A recombinant double stranded DNA molecule according to claim 1, wherein said DNA fragment is linked to the 5' transcriptional regulatory region in anti-sense orientation.

7. A recombinant double stranded DNA molecule according to claim 1, wherein said DNA fragment contains an open reading frame.

8. A recombinant double stranded DNA molecule according to claim 1, wherein said DNA fragment is from a genomic sequence.

9. A recombinant double stranded DNA molecule according to claim 1, wherein said DNA fragment includes an intron.

10. A recombinant double stranded DNA molecule according to claim 1, wherein said DNA fragment includes a non-coding leader sequence.

11. Plasmid pAS, deposited as DSM 6906.

12. Plasmid pAS-GUS, deposited as DSM 6907.

13. A method for the production of transgenic plants that show expression of a desired DNA sequence specifically in guard cells, comprising the steps of:
  a) producing an expression cassette which comprises the following sequences
    i) a 5' transcriptional regulatory region, wherein said 5' transcriptional regulatory region comprises the DNA sequence of Seq I.D. No. 1,
    ii) a first DNA fragment operably linked to said 5' transcriptional regulatory region, and
    iii) a second DNA fragment ensuring termination of transcription and polyadenylation of the resulting transcript,
  b) transferring said expression cassette into plant cells, thereby producing transformed plant cells and
  c) regenerating whole transgenic plants from the transformed cells.

14. A method according to claim 13, wherein said 5' transcriptional regulatory region is isolated from a *Solanum tuberosum* gene coding for ADP glucose pyrophosphorylase.

15. A method according to claim 13, wherein said 5' transcriptional regulatory region is the 3.2 kb HincII/BglII fragment contained in the plasmid pAS, deposited as DSM 6906.

16. A method according to claim 13, wherein said first DNA fragment is linked to the 5' transcriptional regulatory region in sense orientation.

17. A method according to claim 13, wherein said first DNA fragment is linked to the 5' transcriptional regulatory region in anti-sense orientation.

18. A method according to claim 13, wherein said first DNA fragment contains an open reading frame.

19. A method according to claim 13, wherein said first DNA fragment is from a genomic sequence.

20. A method according to claim 13, wherein said first DNA fragment includes an intron.

21. A method according to claim 13, wherein said first DNA fragment includes a non-coding leader sequence.

22. A transgenic plant or plant tissue regenerated from a cell according to claim 13.

23. A plant cell containing a recombinant double stranded DNA molecule according to claim 1.

24. A transgenic plant or plant tissue containing cells according to claim 23.

25. A transgenic plant according to claim 24, wherein said plant is a potato plant.

26. A transgenic plant according to claim 24, wherein said plant is a tomato plant.

27. A transgenic plant according to claim 24, wherein said plant is a tobacco plant.

28. A transgenic plant according to claim 24, wherein said plant is a sugar beet plant.

* * * * *